United States Patent
Lee et al.

(10) Patent No.: US 9,301,911 B2
(45) Date of Patent: Apr. 5, 2016

(54) COMPOSITION COMPRISING TAUROURSODEOXYCHOLIC ACID

(71) Applicant: DAEWOONG PHARMACEUTICAL CO., LTD., Gyeonggi-do (KR)

(72) Inventors: Sang-Ho Lee, Gyeonggi-do (KR); Jun-Hee Lee, Seoul (KR); Hyo-Shin Kim, Incheon (KR); Yeon-Jung Park, Ulsan (KR)

(73) Assignee: DAEWOONG PHARMACEUTICAL CO., LTD., Seongnam-Si (KR)

( * ) Notice: Subject to any disclaimer, the term of this patent is extended or adjusted under 35 U.S.C. 154(b) by 0 days.

(21) Appl. No.: 14/370,327

(22) PCT Filed: Jan. 4, 2013

(86) PCT No.: PCT/KR2013/000036
§ 371 (c)(1),
(2) Date: Jul. 2, 2014

(87) PCT Pub. No.: WO2013/103250
PCT Pub. Date: Jul. 11, 2013

(65) Prior Publication Data
US 2014/0369942 A1      Dec. 18, 2014

(30) Foreign Application Priority Data

Jan. 6, 2012 (KR) .................. 10-2012-0001933

(51) Int. Cl.
| | | |
|---|---|---|
| *A61Q 11/00* | (2006.01) |
| *A61K 45/06* | (2006.01) |
| *A61K 8/19* | (2006.01) |
| *A61K 8/97* | (2006.01) |
| *A61K 8/63* | (2006.01) |
| *A61K 31/575* | (2006.01) |
| *A61K 9/00* | (2006.01) |
| *A61K 36/899* | (2006.01) |
| *A61K 36/9066* | (2006.01) |

(52) U.S. Cl.
CPC ............. *A61K 8/63* (2013.01); *A61K 9/0053* (2013.01); *A61K 31/575* (2013.01); *A61K 36/899* (2013.01); *A61K 36/9066* (2013.01); *A61Q 11/00* (2013.01); *A61K 2800/782* (2013.01)

(58) Field of Classification Search
CPC .... A61K 2300/00; A61K 45/06; A61Q 11/00
See application file for complete search history.

(56) References Cited

U.S. PATENT DOCUMENTS

| | | | | |
|---|---|---|---|---|
| 5,180,575 | A | * | 1/1993 | Ha et al. ........................ 424/49 |
| 5,510,114 | A | * | 4/1996 | Borella et al. ................ 424/452 |
| 5,817,297 | A | | 10/1998 | Ha et al. |
| 2002/0031558 | A1 | | 3/2002 | Yoo |
| 2004/0067204 | A1 | * | 4/2004 | Wolf ............................. 424/49 |
| 2010/0297037 | A1 | * | 11/2010 | Busch ........................... 424/48 |

FOREIGN PATENT DOCUMENTS

| | | |
|---|---|---|
| JP | 2011-21031 A | 2/2011 |
| KR | 10-1998-0076997 A | 11/1998 |
| KR | 10-2000-0012854 A | 3/2000 |
| KR | 10-0333445 B1 | 4/2002 |
| KR | 10-2002-0095594 A | 12/2002 |

OTHER PUBLICATIONS

Hwang et al., "Xanthorrhizol: A Potential Antibacterial Agent from Curcuma xanthorrhiza against *Streptococcus mutans*", Planta Med., vol. 66, pp. 196-197, (2000).

Hwang et al., "Gingivitis suppression effect of the de novo dentifrice containing Curcuma xanthorrhiza, bamboo salt and various additives", J Korean Acad Dent Health, vol. 29, No. 4, pp. 451-462, (2005). English Abstract p. 462.

You et al., "Effects of Bamboo Salt and Bamboo Salt Mixture on the growth, acid production of *Streptococcus mutans*", Journal of Korean Research Association for Purple Bammboo Salt, vol. 1, No. 1, pp. 49-55, (2003). English Abstract p. 49.

* cited by examiner

*Primary Examiner* — Frederick Krass
*Assistant Examiner* — Tracy Liu
(74) *Attorney, Agent, or Firm* — Vorys, Sater, Seymour & Pease LLP; Mih Suhn Koh

(57) ABSTRACT

Provided is a method for preventing or treating a periodontal disease; or a method for improving oral hygiene, including administering a pharmaceutical composition containing tauroursodeoxycholic acid as an active ingredient.

5 Claims, No Drawings

COMPOSITION COMPRISING TAUROURSODEOXYCHOLIC ACID

TECHNICAL FIELD

The present invention relates to a pharmaceutical composition for preventing or treating a periodontal disease; and a composition for improving oral hygiene, comprising tauroursodeoxycholic acid as an active ingredient.

BACKGROUND ART

Periodontal diseases such as dental caries are known as one of the most common chronic diseases in the field of dentistry. Dental caries, which is generally known as 'tooth decay', is a disease caused by gradual irreversible destruction of the hard tissues of the teeth (e.g., enamel, cementum and dentin). Periodontal diseases are induced mainly by bacterial film on the teeth. It is known that numerous microorganisms are present in the bacterial film on the teeth. It has been reported that the microorganisms in bacterial film on the teeth metabolize sugars to form an organic acid, thereby destructing the hard tissues of the teeth. Microorganisms in oral cavity form a biofilm, which is called as dental plaque. Toxic bacteria or toxins produced by them in the dental plaque invade the periodontal tissues to induce gingival inflammation, alveolar bone destruction and infection, which results in periodontal diseases. And also, an acid produced by such bacteria become a cause of dental caries.

As microorganisms inducing periodontal diseases and dental caries in oral cavity, are known *Streptococcus mutans*, *Streptococcus sanguis*, *Actinobacillus viscosus*, *Lactobacillus acidophilus*, etc. It is known that anaerobic microorganisms, among the microorganisms inducing periodontal diseases, produce inflammatory toxins; and therefore it is also important to inhibit or prevent the resulting immune responses. During the progress of inflammation in the periodontal disease, tissue destruction also occurs. When cell walls and tissues are damaged by the stimulus of bacterial endotoxins and other substances, membrane phospholipids in the cell wall are digested by an enzyme to release free arachidonic acid, thereby producing PGE2 and matrix metalloproteinases. Collagenase is one of the representative matrix metalloproteinases. Therefore, it is required in the art to develop an agent having both antimicrobial activity against periodontal disease-inducing bacteria and inhibitory effect against collagenase activity.

Korean Patent No. 10-0333445 has disclosed that ursodeoxycholic acid and/or chenodeoxycholic acid inhibit collagenase activity and thus are useful for an oral hygiene composition for preventing or treating periodontal disease. However, it has not disclosed whether or not ursodeoxycholic acid or chenodeoxycholic acid has an antimicrobial activity against periodontitis-inducing *Streptococcus mutans*, etc.

DISCLOSURE

Technical Problem

The present inventors performed extensive search over various target materials, in order to develop agents having both antimicrobial activity against periodontal disease-inducing bacteria and inhibitory effect against collagenase activity. Surprisingly, it has been newly found by the present invention that tauroursodeoxycholic acid (TUDCA), one of the bile acid derivatives, has both excellent antimicrobial activity against periodontitis-inducing *Streptococcus mutans* and remarkable inhibitory effect against collagenase activity. Especially, it has been newly found that, in comparison with ursodeoxycholic acid, tauroursodeoxycholic acid has about two times more strong inhibitory activity against collagenase at the same concentration.

Therefore, it is an object of the present invention to provide a pharmaceutical composition for treating a periodontal disease or a composition for improving oral hygiene, which comprises tauroursodeoxycholic acid.

Technical Solution

In accordance with an aspect of the present invention, there is provided a pharmaceutical composition for preventing or treating a periodontal disease, which comprises tauroursodeoxycholic acid as an active ingredient.

In accordance with another aspect of the present invention, there is provided a composition for improving oral hygiene, which comprises tauroursodeoxycholic acid as an active ingredient.

In the composition of the present invention, said tauroursodeoxycholic acid may be present in an amount ranging from 0.0001 to 2 wt/wt %, based on the total weight of the composition.

The composition of the present invention may further comprise bamboo salt. Said bamboo salt may be present in an amount ranging from 0.1 to 20 wt/wt %, based on the total weight of the composition. The composition of the present invention may further comprise *xanthorrhiza* oil. Said *xanthorrhiza* oil may be present in an amount ranging from 0.00001 to 0.1 wt/wt %, based on the total weight of the composition.

In an embodiment of the present invention, the composition may further comprise bamboo salt and *xanthorrhiza* oil. In said embodiment, the composition of the present invention may be formulated into a composition where the concentrations in oral cavity of tauroursodeoxycholic acid, bamboo salt and *xanthorrhiza* oil become 0.005 to 0.02 w/v %, 0.8 to 1.3 w/v % and 0.002 to 0.004 w/v %, respectively; preferably 0.01 w/v %, 0.8 to 1.3 w/v % and 0.003 to 0.004 w/v %, respectively.

The composition for improving oral hygiene may be in a form of a paste for dentifrice, a liquid for oral rinse, or a chewing gum.

Advantageous Effects

It has been newly found by the present invention that tauroursodeoxycholic acid, one of the bile acid derivatives, has both excellent antimicrobial activity against periodontitis-inducing *Streptococcus mutans* and remarkable inhibitory effect against collagenase activity. Especially, it has been newly found that tauroursodeoxycholic acid has about two times more strong inhibitory activity against collagenase at the same concentration, in comparison with ursodeoxycholic acid having a similar structure thereto. Therefore, the composition of the present invention can be usefully applied not only for preventing or treating a periodontal disease but also for improving oral hygiene.

BEST MODE

The present invention provides a pharmaceutical composition for preventing or treating a periodontal disease; and a composition for improving oral hygiene, which comprises tauroursodeoxycholic acid as an active ingredient.

Tauroursodeoxycholic acid (TUDCA), which is the conjugate form of ursodeoxycholic acid (UDCA) and taurine, is present in human bile acids and in a bear's gall bladder. TUDCA, along with UDCA, has been widely prescribed as a therapeutic agent in hepatic diseases since a long time ago. Recently, its anti-apoptotic effects for cell survival have been reported in retinal cells, brain cells, cardiac muscle cells, in addition to hepatic cells. There are being performed various researches regarding the UDCA/TUDCA effects on apoptosis-associated degenerative diseases and ischemic diseases. And also, it has been reported that TUDCA inhibits the apoptosis of nerve cells caused by various stimuli.

The present inventors have found that said TUDCA has both excellent antimicrobial activity against periodontitis-inducing *Streptococcus mutans* and remarkable inhibitory effect against collagenase activity. Especially, the present inventors have found that TUDCA has about two times more strong inhibitory activity against collagenase at the same concentration, in comparison with UDCA having a similar structure thereto. Therefore, TUDCA can be usefully applied for a pharmaceutical composition for preventing or treating a periodontal disease, and for a composition for improving oral hygiene. In the composition of the present invention, said TUDCA may be present in an amount ranging from 0.0001 to 2 wt/wt %, preferably from 0.02 to 2 wt/wt %, based on the total weight of the composition.

As used herein, the term "periodontal disease" refers to a disease involving damages in the periodontal ligament and the adjacent tissues, which are caused by bacterial attack on the bottom of the gum line of the V-shaped gap between the gingiva and the teeth. Specifically, said periodontal disease may be one or more selected from the group consisting of gingivitis, periodontitis, and dental caries.

The pharmaceutical composition or the composition for improving oral hygiene of the present invention may contain supplementary ingredients in addition to TUDCA, for example, one or more supplementary ingredients selected from fluoride compounds (e.g., sodium fluoride, sodium fluorophosphate, fluoroamine, tin fluoride, etc.), bamboo salt, chlorhexidine, tranexamic acid, allantoins, caproic acids, enzymes, and extracts of medicinal herbs (*Phellodendri cortex, Platycodi* radix, *Schizonepetae herba, Gardeniae fructus, Glycyrrhizae* radix, *Sanguinaria* radix, etc.). The supplementary ingredients should not adversely affect on the TUDCA activity, i.e., antimicrobial activity against *S. mutans* and inhibitory activity against collagenase.

In an embodiment, the pharmaceutical composition or the composition for improving oral hygiene of the present invention may further comprise bamboo salt and/or *xanthorrhiza* oil, in addition to said TUDCA.

Bamboo salt is the salt obtained by eliminating harmful ingredients through heating salt at high temperature repeatedly. Bamboo salt neutralizes the acid corroding the dental dentin, since it has a strong alkaline pH of 10-11. And also, bamboo salt promotes the growth of harmless oral microorganisms, thereby being able to suppress the microorganisms inducing dental caries and periodontitis (Yongouk You et al., *Journal of Korean Research Association for Purple Bamboo Salt*. Vol. 1. No. 1.49-55, 2003). And also, bamboo salt contains metal ions, such as Zn, Cu, Sn, thereby being able to inhibit acid formation by oral microorganisms. In addition, periodontitis can be treated by its osmotic action. Said bamboo salt may be present in an amount ranging from 0.1 to 20 wt/wt %, preferably 1 to 10 wt/wt %, based on the total weight of the composition.

Xanthorrhiza oil, which is also referred to as 'curcuma *xanthorrhiza* oil', is an oil extracted from the root of *Curcuma xanthorrhiza*, one of the Indonesian medicinal plants, the oil of which is commercially available. *Xanthorrhiza* oil comprises substances such as xanthorrhizol, etc. It has been reported that xanthorrhizol, the major substance, has an excellent antimicrobial effect, especially an excellent antimicrobial effect against the dental caries-causing *S. mutans* (Hwang J K, Shim J S, Baek N I, et al. *Planta Med* 66:196-7 (2000)). Said *xanthorrhiza* oil may be present in an amount ranging from 0.00001 to 0.1 wt/wt %, preferably 0.0001 to 0.1 wt/wt %, based on the total weight of the composition.

Surprisingly, it has been newly found by the present invention that a composition comprising tauroursodeoxycholic acid, bamboo salt, and *xanthorrhiza* oil in a certain amount ratio can accomplish synergistic effects in antimicrobial activity against *Streptococcus mutans*. Therefore, in an embodiment of the present invention, the composition may further comprise bamboo salt and *xanthorrhiza* oil. In said embodiment, the composition of the present invention may be formulated into a composition where the concentrations in oral cavity of tauroursodeoxycholic acid, bamboo salt and *xanthorrhiza* oil become 0.005 to 0.02 w/v %, 0.8 to 1.3 w/v % and 0.002 to 0.004 w/v %, respectively; preferably 0.01 w/v %, 0.8 to 1.3 w/v % and 0.003 to 0.004 w/v %, respectively.

When the composition of the present invention is formulated to a pharmaceutical composition, the composition may be formulated into an oral dosage form such as liquid, suspension, pastes, etc., along with a pharmaceutically acceptable carrier. The pharmaceutically acceptable carrier comprises water, a base material for paste, etc. If necessary, the carrier may comprise sweetening agents and/or flavoring agents. Said TUDCA of the pharmaceutical composition may be orally administered in an effective amount ranging from about 0.01 mg/kg to about 100 mg/kg per day to a patient suffering from periodontal disease. Of course, the dosage may be changed according to constitution of the composition or the patient's age, susceptibility, symptom, etc.

When the composition of the present invention is formulated to a composition for improving oral hygiene, the composition may have the form of a paste for dentifrice (i.e., toothpaste form), a liquid for oral rinse (for example, a gargling liquid form), or a chewing gum, along with conventional additives. For example, in case of preparing a paste for dentifrice, the composition may include conventional additives for toothpaste, such as polishing agents, wetting agents, binding agents, foaming agents, sweetening agents, perfumes, acidity regulating agents, whitening agents, etc., which may be appropriately selected from known literatures. And also, in case of preparing a liquid for oral rinse, the composition may be prepared by dissolving TUDCA and optionally additional supplementary ingredients (for example, bamboo salt, *xanthorrhiza* oil, etc.) in water or an ethanol solution. If necessary, the liquid for oral rinse may include agents for providing refreshing feeling, perfumes, sweetening agents, preservatives, etc.

The present invention will be described in further detail with reference to the following examples. These examples are for illustrative purposes only and are not intended to limit the scope of the present invention.

EXAMPLE 1

Evaluation of Inhibitory Activity on Collagenase

The inhibitory activities of tauroursodeoxycholic acid (TUDCA) and ursodeoxycholic acid (UDCA) on collagenase were evaluated according to an azocoll assay method. Azocoll, Azo dye-impregnated collagen, is not dissolved in Tris-buffer. If azocoll is degraded by collagenase, it shows blue color. Therefore, by reacting said test materials with azocoll and then measuring the respective absorbance, the inhibitory activities of said materials on collagenase can be determined.

2% Azocoll solution (200 μl) and a buffer solution (0.01 M Tris-HCl, 1 mM $CaCl_2$, pH 7.8) (150 μl) were respectively added to the 6 test tubes to obtain the solutions (Solution A1 to A6). Each solution (100 μl) obtained by dissolving TUDCA or UDCA in 10% ethanol in various concentrations was added to the solutions A1 to A6, so as to obtain the final concentrations of 1.600 w/v %, 0.533 w/v %, and 0.178 w/v %, respectively. Collagenase (50 μl) having 100 ppm concentration was added to the respective test mixture, which was then stirred in a 37° C. incubator for 18 hours. Each test tube was centrifuged for 5 minutes. The supernatant was separated from each test tube and then added to a 96-well plate. The absorbance at 540 nm was measured by a spectrophotometer and then the activity of the test group was determined from the standard activity curve. The standard activity curve was separately prepared by adding 10, 25, 50, and 100 μl of collagenase to the azocoll solution.

The collagenase-inhibitory ratio of TUDCA to the collagenase-inhibitory ratio of UDCA was determined according to the following formula and the results thereof are shown in Table 1.

Comparative inhibitory activity=[Collagenase-inhibitory percentage of TUDCA/Collagenase-inhibitory percentage of UDCA]*100

TABLE 1

| Concentration of test material (w/v %) | Comparative inhibitory activity (%) |
|---|---|
| 1.600 | 227.17 |
| 0.533 | 252.56 |
| 0.178 | 264.75 |

From the results of the above Table 1, it can be seen that TUDCA has about 2.3 to 2.6 times strong inhibitory activity against collagenase at the same concentration, in comparison with UDCA.

EXAMPLE 2

Evaluation of Antimicrobial Activity Against S. mutans

We evaluated antimicrobial activities of TUDCA (PRODOTTI CHIMICI E ALIMENTARI S.p.A. Co., Italy), bamboo salt, *xanthorrhiza* oil (curcuma *xanthorrhiza* oil having 22-35% of xanthorrizol, 'Curcuma *Xanthorrhiza* Essential Oil' extracted from Curcuma *Xanthorrhiza* Root, Daewoong Bio Inc.), and a mixture thereof, against S. Mutans. Briefly, to each well of a 96-well plate, were added 100 μl of BHI broth (Brain Heart Infusion broth, Sigma-Aldrich) and each test material in two times higher concentration than the concentration shown in the following Table 2. S. mutans was cultured in BHI broth (Brain Heart Infusion broth, Sigma-Aldrich) at 35° C. for 24 hours. Absorbance at 600 nm of the S. mutans-containing culture medium was adjusted to 0.063 to 0.12 and then the resulting culture medium was diluted to 1/500. The diluted S. Mutans-containing culture medium (100 μl) was added to each well of the 96-well plate. The 96-well plate was incubated at 35° C. for 24 hours, followed by measuring the O.D. values at 600 nm with a spectrophotometer for obtaining the respective growth inhibition percentage. The results thereof are shown in the following Table 2.

TABLE 2

| | TUDCA (w/v %) | Bamboo salt (w/v %) | Xanthorrhiza oil (w/v %) | Growth inhibition (%) |
|---|---|---|---|---|
| 1 | 1% | — | — | 51 ± 13 |
| 2 | 0.5% | — | — | 38 ± 16 |
| 3 | — | 0.5% | — | 0 |
| 4 | — | 0.25% | — | 0 |
| 5 | — | — | 0.007% | 77 ± 18 |
| 6 | — | — | 0.0004% | 0 |
| 7 | 1% | 0.5% | 0.007% | 65 ± 15 |
| 8 | 1% | 0.5% | 0.0004% | 54 ± 5 |
| 9 | 1% | 0.25% | 0.007% | 58 ± 10 |
| 10 | 1% | 0.25% | 0.0004% | 54 ± 11 |
| 11 | 0.5% | 0.5% | 0.007% | 59 ± 30 |
| 12 | 0.5% | 0.5% | 0.0004% | 51 ± 17 |
| 13 | 0.5% | 0.25% | 0.007% | 47 ± 35 |
| 14 | 0.5% | 0.25% | 0.0004% | 63 ± 18 |

From the results of the above Table 2, it can be seen that TUDCA has effective growth-inhibition activity against periodontal disease-inducing S. mutans. And also, it can be seen that, even when TUDCA coexists with other components, such as bamboo salt and *xanthorrhiza* oil, TUDCA still maintains the growth-inhibition activity against S. mutans. Therefore, TUDCA has excellent antimicrobial activity against *Streptococcus mutans*, as well as remarkable inhibitory effect against collagenase activity. Accordingly, it is expected that TUDCA can be usefully applied to a composition for treating a periodontal disease and to a composition for improving oral hygiene.

EXAMPLE 3

Evaluation of Synergistic Activity

Antimicrobial activities against S. mutans were evaluated using TUDCA in a relatively low concentration. Using the same kinds of TUDCA, bamboo salt, and *xanthorrhiza* oil, the evaluations of antimicrobial activity were carried out in the same manners as in Example 2. The results thereof are shown in the following Table 3.

TABLE 3

| | TUDCA (w/v %) | Bamboo salt (w/v %) | Xanthorrhiza oil (w/v %) | Growth inhibition (%) |
|---|---|---|---|---|
| 1 | 0.01% | — | — | 13 |
| 2 | — | 1.3% | — | 47 |
| 3 | — | 0.8% | — | 7 |
| 4 | — | — | 0.004% | 54 |
| 5 | — | — | 0.003% | 19 |
| 6 | 0.01% | 1.3% | 0.003% | 99 |
| 7 | 0.01% | 0.8% | 0.004% | 99 |
| 8 | 0.01% | 0.8% | 0.003% | 52 |

From the results of the above Table 3, it can be seen that the groups containing TUDCA in a relatively low amount (about 0.01 w/v %) along with bamboo salt and *xanthorrhiza* oil showed remarkable synergistic effects in growth-inhibition activity against S. mutans. Therefore, if applied to the oral cavity, the composition of the present invention may be formulated into a composition where the concentrations in oral cavity of tauroursodeoxycholic acid, bamboo salt and *xanthorrhiza* oil become 0.005 to 0.02 w/v %, 0.8 to 1.3 w/v % and 0.002 to 0.004 w/v %, respectively; preferably 0.01 w/v %, 0.8 to 1.3 w/v % and 0.003 to 0.004 w/v %, respectively.

Formulation 1: Preparation of Toothpaste

| | |
|---|---|
| calcium phosphate dibasic | 40.0 w/v % |
| sorbitol | 30.0 w/v % |
| sodium lauryl sulfate | 1.5 w/v % |
| saccharin sodium | 0.1 w/v % |
| sodium para-hydroxybenzoate | 1.0 w/v % |
| sodium carboxymethyl cellulose | 1.0 w/v % |
| TUDCA | 1.0 w/v % |
| sodium monofluorophosphate | 0.76 w/v % |
| Purified water was added to | 100 w/v % in total. |

Formulation 2: Preparation of Toothpaste

| | |
|---|---|
| calcium phosphate dibasic | 40.0 w/v % |
| sorbitol | 30.0 w/v % |
| sodium lauryl sulfate | 1.5 w/v % |
| saccharin sodium | 0.1 w/v % |
| sodium para-hydroxybenzoate | 1.0 w/v % |
| sodium carboxymethyl cellulose | 1.0 w/v % |
| TUDCA | 0.5 w/v % |
| bamboo salt | 0.25 w/v % |
| sodium monofluorophosphate | 0.76 w/v % |
| Purified water was added to | 100 w/v % in total. |

Formulation 3: Preparation of Toothpaste

| | |
|---|---|
| calcium phosphate dibasic | 40.0 w/v % |
| sorbitol | 30.0 w/v % |
| sodium lauryl sulfate | 1.5 w/v % |
| saccharin sodium | 0.1 w/v % |
| sodium para-hydroxybenzoate | 1.0 w/v % |
| sodium carboxymethyl cellulose | 1.0 w/v % |
| TUDCA | 0.5 w/v % |
| xanthorrhiza oil | 0.0004 w/v % |
| sodium monofluorophosphate | 0.76 w/v % |
| Purified water was added to | 100 w/v % in total. |

Formulation 4: Preparation of Toothpaste

| | |
|---|---|
| calcium phosphate dibasic | 40.0 w/v % |
| sorbitol | 30.0 w/v % |
| sodium lauryl sulfate | 1.5 w/v % |
| saccharin sodium | 0.1 w/v % |
| sodium para-hydroxybenzoate | 1.0 w/v % |
| sodium carboxymethyl cellulose | 1.0 w/v % |
| TUDCA | 0.5 w/v % |
| bamboo salt | 0.25 w/v % |
| xanthorrhiza oil | 0.0004 w/v % |
| sodium monofluorophosphate | 0.76 w/v % |
| Purified water was added to | 100 w/v % in total. |

The invention claimed is:

1. A method for treating or preventing a periodontal disease in a subject in need thereof comprising administering to the subject a pharmaceutical composition comprising tauroursodeoxycholic acid, bamboo salt and *xanthorrhiza* oil as active ingredients, the periodontal disease being selected from the group consisting of gingivitis, periodontitis and dental caries, wherein the pharmaceutical composition is administered to the oral cavity of the subject and the concentrations of tauroursodeoxycholic acid, bamboo salt and *xanthorrhiza* oil are, respectively, 0.005 to 0.02 w/v %, 0.8 to 1.3 w/v % and 0.002 to 0.004 w/v %.

2. The method of claim 1, wherein the concentrations of tauroursodeoxycholic acid, bamboo salt and *xanthorrhiza* oil are, respectively, 0.01 w/v %, 0.8 to 1.3 w/v % and 0.003 to 0.004 w/v %.

3. A method for improving oral hygiene in a subject in need thereof comprising administering to the subject a hygienic composition comprising tauroursodeoxycholic acid, bamboo salt and *xanthorrhiza* oil as active ingredients, wherein the hygienic composition is administered to the oral cavity of the subject and the concentrations of tauroursodeoxycholic acid, bamboo salt and *xanthorrhiza* oil are, respectively, 0.005 to 0.02 w/v %, 0.8 to 1.3 w/v % and 0.002 to 0.004 w/v % in the oral cavity.

4. The method of claim 3, wherein the concentrations of tauroursodeoxycholic acid, bamboo salt and *xanthorrhiza* oil are, respectively, 0.01 w/v %, 0.8 to 1.3 w/v % and 0.003 to 0.004 w/v %.

5. The method of claim 3, wherein the hygienic composition is a paste for dentifrice, a liquid for oral rinse, or a chewing gum.

* * * * *